United States Patent
Yuhas et al.

(10) Patent No.: US 10,493,424 B2
(45) Date of Patent: Dec. 3, 2019

(54) CRYSTALLINE METALLOPHOSPHATES, THEIR METHOD OF PREPARATION, AND USE

(71) Applicant: UOP LLC, Des Plaines, IL (US)

(72) Inventors: Benjamin D. Yuhas, Evanston, IL (US); Mark A. Miller, Niles, IL (US); Melissa M. Galey, Chicago, IL (US); John P. S. Mowat, Arlington Heights, IL (US); Wharton Sinkler, Des Plaines, IL (US)

( * ) Notice: Subject to any disclaimer, the term of this patent is extended or adjusted under 35 U.S.C. 154(b) by 0 days.

(21) Appl. No.: 16/036,709

(22) Filed: Jul. 16, 2018

(65) Prior Publication Data

US 2019/0030511 A1     Jan. 31, 2019

Related U.S. Application Data

(60) Provisional application No. 62/538,403, filed on Jul. 28, 2017.

(51) Int. Cl.
| | |
|---|---|
| *B01J 20/02* | (2006.01) |
| *B01J 20/18* | (2006.01) |

(Continued)

(52) U.S. Cl.
CPC ........... *B01J 20/0292* (2013.01); *B01J 20/18* (2013.01); *B01J 29/85* (2013.01); *B01J 35/002* (2013.01); *C01B 37/04* (2013.01); *C01B 39/54* (2013.01); *C07C 1/20* (2013.01); *C07C 5/02* (2013.01); *C07C 5/224* (2013.01); *C07C 5/2716* (2013.01); *C07C 2529/83* (2013.01)

(58) Field of Classification Search
None
See application file for complete search history.

(56) References Cited

U.S. PATENT DOCUMENTS

| | | |
|---|---|---|
| 4,310,440 A | 1/1982 | Wilson et al. |
| 4,440,871 A | 4/1984 | Lok et al. |

(Continued)

FOREIGN PATENT DOCUMENTS

| | | |
|---|---|---|
| EP | 2867166 B1 | 3/2017 |

OTHER PUBLICATIONS

Smith et al., Enumeration of 4-connected 3-dimensional nets and classification of framework silicates: the infinite set of ABC-6 nets; the Archimedian and σ-related nets; American Mineralogist, vol. 66, pp. 777-788, 1981.

(Continued)

*Primary Examiner* — Clinton A Brooks

(57) ABSTRACT

A new family of crystalline microporous metallophosphates designated AlPO-78 has been synthesized. These metallophosphates are represented by the empirical formula $$R^+_r M_m^{2+} E P_x Si_y O_z$$

where R is an organoammonium cation, M is a framework metal alkaline earth or transition metal of valence +2, and E is a trivalent framework element such as aluminum or gallium. The AlPO-78 compositions are characterized by a new unique ABC-6 net structure, and have catalytic properties suitable for carrying out various hydrocarbon conversion processes, as well as characteristics suitable for the efficient adsorption of water vapor in a variety of applications, such as adsorption heat pumps.

18 Claims, 4 Drawing Sheets

(51) Int. Cl.
*B01J 29/85* (2006.01)
*C01B 37/04* (2006.01)
*C07C 5/02* (2006.01)
*C07C 5/22* (2006.01)
*C07C 5/27* (2006.01)
*C07C 1/20* (2006.01)
*C01B 39/54* (2006.01)
*B01J 35/00* (2006.01)

(56) References Cited

U.S. PATENT DOCUMENTS

| | | | |
|---|---|---|---|
| 4,567,029 | A | 1/1986 | Wilson et al. |
| 4,973,785 | A | 11/1990 | Lok et al. |
| 5,126,308 | A | 6/1992 | Barger et al. |
| 7,422,993 | B2 | 9/2008 | Takewaki et al. |
| 8,569,557 | B1 | 10/2013 | Lewis et al. |
| 8,906,225 | B2 | 12/2014 | Lewis et al. |
| 8,911,614 | B2 | 12/2014 | Lewis et al. |
| 9,517,942 | B2 | 12/2016 | Chen et al. |
| 9,522,896 | B2 | 12/2016 | Nicholas et al. |
| 9,811,614 | B2 * | 11/2017 | Jacobs ............... G06F 17/5009 |

OTHER PUBLICATIONS

Xie et al., "SSZ-52, a Zeolite with an 18-Layer Aluminosilicate Framework Structure RElated to That of the DeNOx catalyst Cu-SSZ-13", Journal of the American Chemical Society, 2013, 135, 10519-10524, 2013.

Van Heyden, Kinetics of Water Adsorption in Microporous Aluminophosphate layers for regenerative heat exchangers, Applied Thermal Engineering, 29 (2009) 1514-1522.

Wright et al., Cation-directed syntheses of novel zeolite-like metalloaluminophosphates STA-6 and STA-7 in the presence of azamacrocycle templates, J. Chem. Sc=oc., Dalton Trans., 2000, pp. 1243-1248.

Schreyeck et al., The diaza-polyoxa-macrocycle 'Kryptofix222' as a new template for the synth esis of LTA-type~AlPO4 Co-templating role of F and/or (CH3)4N+ ions, Micorporous and Mesoporous Materials 22 (1998) 87-106.

De Lange et al., Adsorption-Driven Heat Pumps: The Potential of Metal-Organic Frameworks, Chem. Rev. 2015, 115, 12205-12250, American Chemical Society.

International Search Report for International application No. PCT/US2018/043354 dated Oct. 18, 2018.

* cited by examiner

CRYSTALLINE METALLOPHOSPHATES, THEIR METHOD OF PREPARATION, AND USE

CROSS-REFERENCE TO RELATED APPLICATION

This application claims priority from Provisional Application No. 62/538,403 filed Jul. 28, 2017, the contents of which cited application are hereby incorporated by reference in its entirety.

BACKGROUND OF THE INVENTION

This invention relates to a novel family of metallophosphates, collectively designated AlPO-78. They are represented by the empirical formula:

$$R^+_r M^{2+}_m EP_x Si_y O_z$$

where M is a divalent framework metal such as magnesium or zinc, R is an organoammonium cation, and E is a trivalent framework element such as aluminum or gallium.

Classes of molecular sieves include crystalline aluminophosphate, silicoaluminophosphate, or metalloaluminophosphate compositions which are microporous and which are formed from corner sharing $AlO_{4/2}$ and $PO_{4/2}$ tetrahedra. In 1982, Wilson et al. first reported aluminophosphate molecular sieves, the so-called AlPOs, which are microporous materials that have many of the same properties as zeolites, although they do not contain silica (see U.S. Pat. No. 4,310,440). Subsequently, charge was introduced to the neutral aluminophosphate frameworks via the substitution of $SiO_{4/2}$ tetrahedra for $PO_{4/2}^+$ tetrahedra to produce the SAPO molecular sieves as described by Lok et al. (see U.S. Pat. No. 4,440,871). Another way to introduce framework charge to neutral aluminophosphates is to substitute $[Me^{2+}O_{4/2}]^{2-}$ tetrahedra for $AlO_{4/2}^-$ tetrahedra, which yields the MeAPO molecular sieves (see U.S. Pat. No. 4,567,029). It is furthermore possible to introduce framework charge on AlPO-based molecular sieves via the simultaneous introduction of $SiO_{4/2}$ and $[M^{2+}O_{4/2}]^{2-}$ tetrahedra to the framework, giving MeAPSO molecular sieves (see U.S. Pat. No. 4,973,785).

Numerous molecular sieves, both naturally occurring and synthetically prepared, are used in various industrial processes. Synthetically, these molecular sieves are prepared via hydrothermal synthesis employing suitable sources of Si, Al, P, metals, and structure directing agents such as amines or organoammonium cations. The structure directing agents reside in the pores of the molecular sieve and are largely responsible for the particular structure that is ultimately formed. These species may balance the framework charge associated with silicon or other metals such as Zn or Mg in the aluminophosphate compositions, and can also serve as space fillers to stabilize the tetrahedral framework. Molecular sieves are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent molecular sieve crystal structure. Molecular sieves can be used as catalysts for hydrocarbon conversion reactions, which can take place on outside surfaces as well as on internal surfaces within the pore.

As stated above, molecular sieves are capable of reversibly adsorbing and desorbing certain molecules depending on the adsorbate's size and the molecular sieve's internal pore structure. There are many applications where it is desired to adsorb water vapor, preferably in a reversible manner. One such application is an adsorption heat pump, which is a device that can be used to recover energy from exhaust or waste heat. As such, adsorption heat pumps can be utilized to maximize energy efficiency in an environmentally friendly manner. Molecular sieves can be useful materials to act as water vapor adsorbents in an adsorption heat pump due to their high capacity for water vapor. A description of the use of adsorbents in adsorption heat pumps can be found in U.S. Pat. No. 8,323,747, incorporated by reference herein in its entirety.

The type of molecular sieves used in adsorption heat pumps must meet certain requirements for optimal performance. A high overall capacity for water vapor is important, but most critically, they should fully desorb all adsorbed water at no greater than 100° C. Otherwise, too much heat must be applied to fully remove the adsorbed water from the micropores (i.e., the regeneration temperature is too high), thus requiring too high of an energy input. The majority of aluminosilicates (i.e., zeolites) have rapid uptake of water vapor at very low pressures ($P/P_0$), which conversely leads to an unacceptably high regeneration temperature, despite a high overall capacity for water vapor. Aluminophosphates and silicoaluminophosphates have been shown to have more favorable adsorption characteristics for water vapor (see, for example, M. F. de Lange et al. CHEM. REV. 115, 12205 (2015); H. van Heyden et al. APPL. THERM. ENG. 29, 1514 (2009). In particular, the materials SAPO-34 and SAPO-5 (zeotypes CHA and AFI, respectively) have been shown to have particular utility as adsorbent materials in adsorption heat pumps (see U.S. Pat. Nos. 7,422,993 and 9,517,942).

SUMMARY OF THE INVENTION

As stated, the present invention relates to a new family of metallophosphate molecular sieves, collectively designated AlPO78. Accordingly, one embodiment of the invention is a microporous crystalline material having a three-dimensional framework of at least $EO_{4/2}^-$ and $PO_{4/2}^+$ tetrahedral units and optionally, at least one of $[M^{2+}O_{4/2}]^{2-}$ and $SiO_{4/2}$ tetrahedral units and an empirical composition in the as-synthesized form and anhydrous basis expressed by an empirical formula of:

$$R^+_r M^{2+}_m EP_x Si_y O_z$$

where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, and R is an organoammonium cation. "r" is the mole ratio of R to E and has a value of about 0.1 to about 2.0, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, and "z" is the mole ratio of O to E and has a value determined by the equation:

$$z = (2 \cdot m + r + 3 + 5 \cdot x + 4 \cdot y)/2$$

The invention is characterized in that it has the x-ray diffraction pattern having at least the d-spacings and intensities set forth in Table 1:

TABLE 1

| 2-Theta | d(Å) | Intensity |
|---|---|---|
| 7.88-7.98 | 11.21-11.07 | m-s |
| 8.15-8.50 | 10.84-10.39 | m-s |
| 8.82-9.05 | 10.01-9.76 | s |
| 9.67-9.96 | 9.14-8.87 | s-vs |
| 10.58-10.81 | 8.35-8.17 | m |
| 10.92-11.71 | 8.09-7.55 | m-s |
| 13.21-13.67 | 6.69-6.47 | s |
| 14.10-14.54 | 6.27-6.08 | s-vs |
| 15.48-16.02 | 5.72-5.53 | m |
| 16.05-16.24 | 5.52-5.45 | s |
| 16.44-16.81 | 5.39-5.28 | m |
| 16.87-17.01 | 5.25-5.21 | m-s |
| 17.19-17.43 | 5.15-5.08 | s |
| 17.78-18.46 | 4.98-4.80 | s-vs |
| 18.73-19.22 | 4.73-4.61 | vw-w |
| 19.48-19.86 | 4.55-4.47 | w-m |
| 20.47-20.96 | 4.33-4.23 | s |
| 21.00-21.45 | 4.23-4.14 | m-s |
| 21.52-21.73 | 4.12-4.08 | m-s |
| 21.88-22.10 | 4.06-4.02 | s |
| 22.15-22.42 | 4.01-3.96 | m-s |
| 22.52-22.95 | 3.94-3.87 | w-m |
| 23.14-23.52 | 3.84-3.78 | w-m |
| 23.58-23.71 | 3.77-3.75 | s |
| 23.75-24.01 | 3.74-3.70 | w-m |
| 24.75-24.93 | 3.59-3.57 | w-m |
| 25.01-25.47 | 3.56-3.49 | vs |
| 26.15-26.31 | 3.40-3.38 | w-m |
| 26.37-26.54 | 3.38-3.35 | m |
| 26.78-27.02 | 3.33-3.30 | w-m |
| 27.11-27.40 | 3.29-3.25 | m |
| 28.39-28.86 | 3.14-3.09 | w-m |
| 29.22-29.65 | 3.05-3.01 | m |
| 30.60-30.95 | 2.92-2.89 | w-m |
| 31.62-31.93 | 2.83-2.80 | w-m |
| 31.97-32.28 | 2.80-2.77 | w-s |
| 32.44-32.89 | 2.76-2.72 | w-m |
| 33.19-33.40 | 2.70-2.68 | vw-w |
| 33.51-33.82 | 2.67-2.65 | w-m |
| 34.72-35.08 | 2.58-2.55 | vw-w |

Another embodiment of the invention is a microporous crystalline material having a three-dimensional framework of at least $EO_{4/2}^-$ and $PO_{4/2}^+$ tetrahedral units and optionally, at least one of $[M^{2+}O_{4/2}]^{2-}$ and $SiO_{4/2}$ tetrahedral units and an empirical composition in the calcined form and anhydrous basis expressed by an empirical formula of:

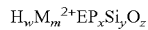

$$H_w M_m^{2+} E P_x Si_y O_z$$

where "m", "x", "y" are as described above, H is a proton, "w" is the mole ratio of H to E and varies from 0 to 2.5, and "z" is the mole ratio of O to E and has a value determined by the equation:

$$z=(w+2\cdot m+3+5\cdot x+4\cdot y)/2$$

and the invention is characterized in that it has the x-ray diffraction pattern having at least the d-spacings and intensities set forth in Table 2:

TABLE 2

| 2-Theta | d(Å) | Intensity |
|---|---|---|
| 8.02-8.12 | 11.01-10.88 | w |
| 8.40-8.51 | 10.51-10.38 | m |
| 8.63-8.73 | 10.23-10.12 | w-m |
| 9.78-9.89 | 9.03-8.93 | m-s |
| 10.70-10.81 | 8.26-8.17 | m-s |
| 12.83-12.95 | 6.89-6.82 | vw |
| 13.71-13.86 | 6.45-6.38 | vs |
| 14.00-14.13 | 6.32-6.26 | m-s |
| 16.16-16.64 | 5.48-5.32 | vw-w |
| 16.92-17.05 | 5.23-5.19 | vw-w |

TABLE 2-continued

| 2-Theta | d(Å) | Intensity |
|---|---|---|
| 17.44-17.56 | 5.08-5.04 | m |
| 17.79-17.93 | 4.98-4.94 | m-s |
| 19.68-19.89 | 4.51-4.46 | w |
| 20.43-20.61 | 4.34-4.30 | w-m |
| 21.17-21.35 | 4.19-4.16 | w-m |
| 21.81-21.99 | 4.07-4.04 | m-s |
| 22.15-22.53 | 4.01-3.94 | m-s |
| 22.55-22.74 | 3.94-3.91 | w-m |
| 23.95-24.25 | 3.71-3.67 | m-s |
| 24.57-24.79 | 3.62-3.59 | m-s |
| 25.87-26.31 | 3.44-3.38 | w-m |
| 26.49-26.71 | 3.36-3.33 | m |
| 27.40-27.88 | 3.25-3.20 | m-s |
| 28.32-28.52 | 3.15-3.13 | m-s |
| 28.85-29.02 | 3.09-3.07 | vw-w |
| 29.40-29.63 | 3.03-3.01 | w-m |
| 29.71-29.93 | 3.00-2.98 | vw |
| 30.28-30.44 | 2.95-2.93 | vw-w |
| 31.21-31.38 | 2.86-2.85 | vw-w |
| 32.18-32.50 | 2.79-2.75 | w-m |
| 32.65-32.92 | 2.74-2.72 | w-m |
| 33.00-33.15 | 2.71-2.70 | w-m |
| 34.25-34.41 | 2.61-2.60 | vw-w |
| 35.16-35.35 | 2.55-2.54 | w-m |

Another embodiment of the invention is a process for preparing the crystalline microporous metallophosphate molecular sieve described above. The process comprises forming a reaction mixture containing reactive sources of R, E, P, one or both of M and Si, and heating the reaction mixture at a temperature of about 60° C. to about 200° C. for a time sufficient to form the molecular sieve, the reaction mixture having a composition expressed in terms of mole ratios of the oxides of:

$$aR_2O{:}bMO{:}E_2O_3{:}cP_2O_5{:}dSiO_2{:}eH_2O$$

where "a" has a value of about 0.75 to about 12, "b" has a value of about 0 to about 2, "c" has a value of about 0.5 to about 8, "d" has a value of about 0 to about 4, and "e" has a value from 30 to 1000.

Yet another embodiment of the invention is a hydrocarbon conversion process using the above-described molecular sieve as a catalyst. The process comprises contacting at least one hydrocarbon with the molecular sieve at conversion conditions to generate at least one converted hydrocarbon.

Still another embodiment of the invention is an adsorption process using the crystalline AlPO-78 material. The process may involve the adsorption and desorption of water vapor over AlPO-78 in an adsorption heat pump-type apparatus. Separation of molecular species can be based either on the molecular size (kinetic diameter) or on the degree of polarity of the molecular species. Removing contaminants may be by ion exchange with the molecular sieve.

DETAILED DESCRIPTION OF THE INVENTION

Figure 1:
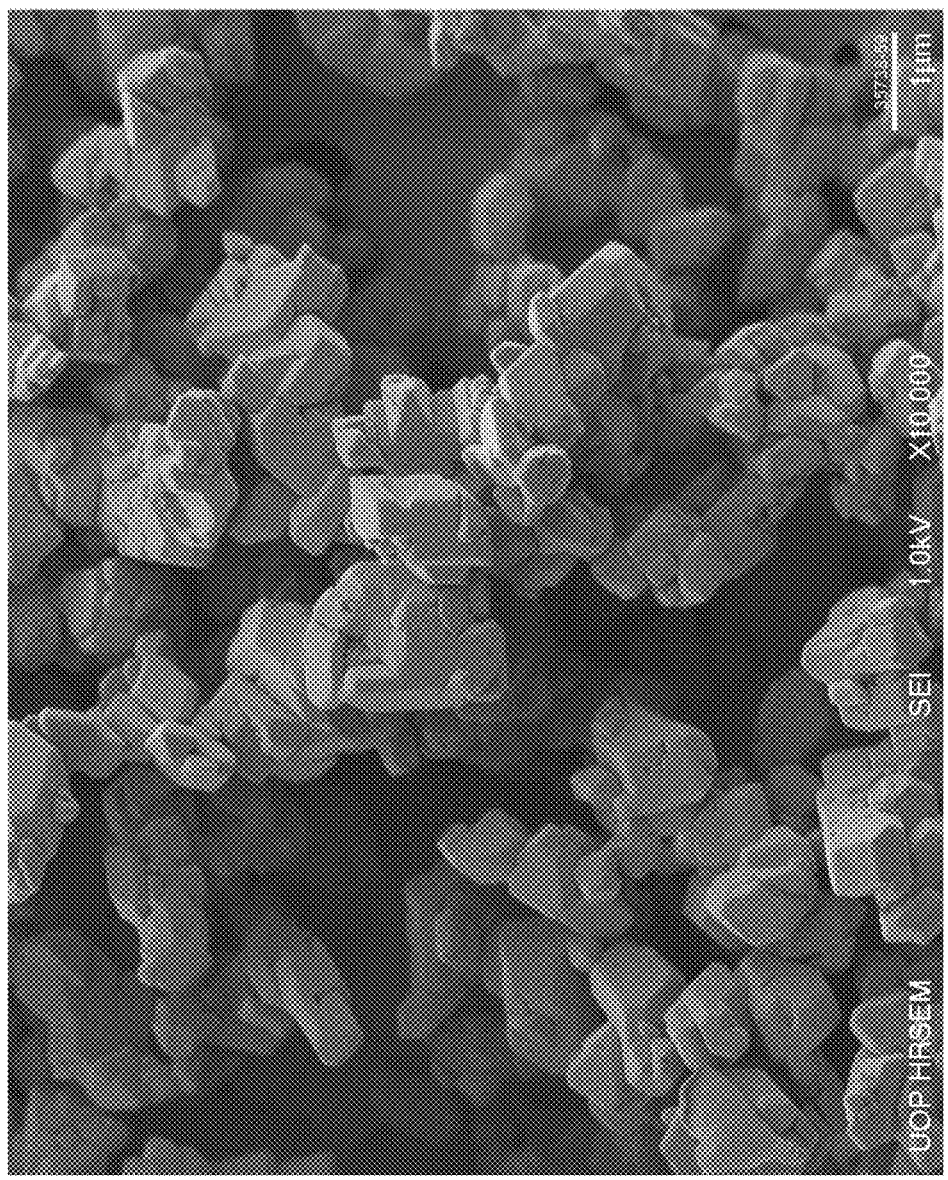
FIG. 1 is a scanning electron microscope (SEM) image of an exemplary AlPO-78 material according to an embodiment described herein.

Applicants have prepared a family of metallophosphate materials whose topological structure is unique. In their paper "Enumeration of 4-connected 3-dimensional nets and classification of framework silicates: the infinite set of ABC-6 nets; the Archimedean and σ-related nets," Smith and Bennett state "To a first approximation, all silicates belonging to the ABC-6net family have x-ray diffraction patterns which can be indexed on a hexagonal prismatic unit cell with lattice parameters a ~13.0±0.3 Å and c~p×(2.6±0.1 Å)" (see AMERICAN MINERALOGIST, 66, 777-788 (1981)). This finding has subsequently been confirmed by others (see, for example, D. Xie et al. J. AM. CHEM. SOC. 135, 10519 (2013)) as the ABC-6 family has expanded.

One particular composition of AlPO-78 indexes on a unit cell with hexagonal axes with lattice parameters a=12.768 Å and c=60.825 Å, which is suggests an ABC-6 net structure with the stacking sequence repeating every 24 layers along the c-axis (p=60.825/2.5=24.33). This is the first known example of an ABC-6 net structure with 24-layer repeats, and would be the largest repeat unit ever reported in a synthetic ABC-6 net molecular sieve. Hence the topology of AlPO-78 family of materials is unique. The instant microporous crystalline material (AlPO-78) has an empirical composition in the as-synthesized form and on an anhydrous basis expressed by the empirical formula:

$$R^+_r M_m^{2+} E P_x Si_y O_z$$

where M is at least one framework divalent cation and is selected from the group consisting of alkaline earth and transition metals. Specific examples of the M cations include but are not limited to beryllium, magnesium, cobalt (II), manganese, zinc, iron (II), nickel and mixtures thereof. R is an organoammonium cation. "r" is the mole ratio of R to E and varies from about 0.1 to about 2.0. The value of "m" is the mole ratio of M to E and varies from 0 to about 1.0, "x" is mole ratio of P to E and varies from 0.5 to about 2.0. The ratio of silicon to E is represented by "y" which varies from about 0 to about 1.0. E is a trivalent element which is tetrahedrally coordinated, is present in the framework, and is selected from the group consisting of aluminum, gallium, iron (III) and boron. Lastly, "z" is the mole ratio of O to E and is given by the equation:

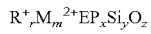

$$z=(2 \cdot m+r+3+5 \cdot x+4 \cdot y)/2.$$

Synthesis of molecular sieve materials often relies on the use of organoamino or organoammonium templates known as organic structure directing agents (OSDAs). While simple OSDAs such as tetramethylammonium, tetraethylammonium and tetrapropylammonium are commercially available, oftentimes OSDAs are complicated molecules that are difficult and expensive to synthesize. However, their importance lies in their ability to impart aspects of their structural features to the molecular sieve to yield a desirable pore structure. For example, the use of 1,4,7,10,13,16-hexamethyl-1,4,7,10,13,16-hexaazacyclooctadecane as OSDA has been shown to allow synthesis of STA-7, an aluminophosphate based material of the SAV zeotype (Wright et.al. J. CHEM. SOC., Dalton Trans., 2000, 1243-1248); the use of 4,7,13,16,21,24-hexaoxa-1,10-diazabicyclo[8.8.8]hexacosane ('Kryptofix 222') led to the synthesis of AlPO₄-42 (Schreyeck et.al. MICRO. MESO. MATER. 1998, 22, 87-106); MAPO-35, a magnesium aluminophosphate material with the LEV topology, is disclosed in U.S. Pat. No. 4,567,029 in which quinuclidine is employed as a structure directing agent; and in U.S. Pat. No. 4,973,785, the MeAPSO composition CoAPSO-35 is disclosed, which contains both cobalt and silicon in the framework in addition to Al and P and uses methylquinuclidine as the structure directing agent.

The art clearly shows that use of complex organoammonium SDAs often results in new molecular sieve materials. However, the synthesis of these complicated organoammonium compounds is quite lengthy and requires many steps, often in an organic solvent, thereby hindering development of the new molecular sieve material. Frequently, even for simple, commercially available OSDAs, the OSDA is the most costly ingredient used in synthesizing molecular sieve materials. Consequently, it would be economically advantageous to synthesize new molecular sieves from either commercially available organoammonium SDAs or SDAs which may be readily synthesized from commercially available starting materials. This has recently been demonstrated in an elegant fashion using simple aqueous chemistry to generate a novel family of organo-1-oxa-4-azonium cyclohexane compounds (U.S. Pat. No. 9,522,896), derived from morpholino-based compounds. The procedures described in U.S. Pat. No. 9,522,896 can be extended to the family of piperidine-based compounds as well. This procedure thereby allows the preparation of SDAs, such as unusual quaternary ammonium salts, from readily available starting reagents in a facile and practical manner. OSDAs prepared by the methods of the present invention are in aqueous solution and do not pose odor and flashpoint concerns. The result is the unprecedented ability to remove the cooling step typically required in the preparation of in-situ zeolite reaction mixtures and to avoid purification steps such as evaporation of organic solvent typically required in ex-situ preparation methods. The obtained organoammonium bromide salt can be ion-exchanged, either by reaction with Ag₂O or by anion exchange resins to yield the hydroxide form of the organoammonium compound, or used as the halogen salt directly. Finally, the resultant organoammonium compound can be used for the synthesis of a zeolite or molecular sieve.

The microporous crystalline metallophosphate AlPO-78 is prepared by a hydrothermal crystallization of a reaction mixture prepared by combining reactive sources of R, E, phosphorus, and one or both of M and silicon. A preferred form of the AlPO-78 materials is when E is Al. The sources of aluminum include but are not limited to aluminum alkoxides, precipitated aluminas, aluminum metal, aluminum hydroxide, aluminum salts and alumina sols. Specific examples of aluminum alkoxides include, but are not limited to aluminum ortho sec-butoxide and aluminum ortho isopropoxide. Sources of phosphorus include, but are not limited to, orthophosphoric acid, phosphorus pentoxide, and ammonium dihydrogen phosphate. Sources of silica include but are not limited to tetraethylorthosilicate, colloidal silica, and precipitated silica. Sources of the other E elements include but are not limited to organoammonium borates, boric acid, precipitated gallium oxyhydroxide, gallium sulfate, ferric sulfate, and ferric chloride. Sources of the M metals include the halide salts, nitrate salts, acetate salts, and sulfate salts of the respective alkaline earth and transition metals. R is an organoammonium cation prepared from the reaction of an aqueous mixture of a cyclic secondary amine and an organic dihalide. Specific examples of cyclic secondary amines include, without limitation, piperidine, homopiperidine, pyrrolidine, and morpholine. Specific examples of organic dihalides include, without limitation, 1,4-dibromobutane, 1,5-dibromopentane, and 1,6-dibromohexane.

In one embodiment, the cyclic secondary amine is piperidine and the organic dihalide is 1,4-dibromobutane. In another embodiment, the cyclic secondary amine is piperidine and the organic dihalide is 1,4-dibromopentane. In another embodiment, the cyclic secondary amine is piperidine and the organic dihalide is 1,5-dibromopentane. In another embodiment, the cyclic secondary amine is pyrrolidine and the organic dihalide is 1,4-dibromobutane.

The reaction mixture containing reactive sources of the desired components can be described in terms of molar ratios of the oxides by the formula:

$$aR_2O:bMO:E_2O_3:cP_2O_5:dSiO_2:eH_2O$$

where "a" has a value of about 0.75 to about 12, "b" has a value of about 0 to about 2, "c" has a value of about 0.5 to about 8, "d" has a value of about 0 to about 4, and "e" has a value from 30 to 1000. If alkoxides are used, it is preferred to include a distillation or evaporative step to remove the alcohol hydrolysis products.

The reaction mixture is reacted at a temperature of about 60° C. to about 200° C. and preferably from about 125° C. to about 175° C. for a period of about 1 day to about 21 days and preferably for a time of about 2 days to about 10 days in a sealed reaction vessel at autogenous pressure. The reaction vessel may be heated with stirring, heated while tumbling, or heated quiescently. After crystallization is complete, the solid product is isolated from the heterogeneous mixture by means such as filtration or centrifugation, and then washed with deionized water and dried in air at ambient temperature up to about 100° C. AlPO-78 seeds can optionally be added to the reaction mixture in order to accelerate the formation of the desired microporous composition.

The AlPO-78 aluminophosphate-based material, which is obtained from the above-described process, is characterized by the x-ray following diffraction pattern, having at least the d-spacings and relative intensities set forth in Table 1:

TABLE 1

| 2-Theta | d(Å) | Intensity |
|---|---|---|
| 7.88-7.98 | 11.21-11.07 | m-s |
| 8.15-8.50 | 10.84-10.39 | m-s |
| 8.82-9.05 | 10.01-9.76 | s |
| 9.67-9.96 | 9.14-8.87 | s-vs |
| 10.58-10.81 | 8.35-8.17 | m |
| 10.92-11.71 | 8.09-7.55 | m-s |
| 13.21-13.67 | 6.69-6.47 | s |
| 14.10-14.54 | 6.27-6.08 | s-vs |
| 15.48-16.02 | 5.72-5.53 | m |
| 16.05-16.24 | 5.52-5.45 | s |
| 16.44-16.81 | 5.39-5.28 | m |
| 16.87-17.01 | 5.25-5.21 | m-s |
| 17.19-17.43 | 5.15-5.08 | s |
| 17.78-18.46 | 4.98-4.80 | s-vs |
| 18.73-19.22 | 4.73-4.61 | vw-w |
| 19.48-19.86 | 4.55-4.47 | w-m |
| 20.47-20.96 | 4.33-4.23 | s |
| 21.00-21.45 | 4.23-4.14 | m-s |
| 21.52-21.73 | 4.12-4.08 | m-s |
| 21.88-22.10 | 4.06-4.02 | s |
| 22.15-22.42 | 4.01-3.96 | m-s |
| 22.52-22.95 | 3.94-3.87 | w-m |
| 23.14-23.52 | 3.84-3.78 | w-m |
| 23.58-23.71 | 3.77-3.75 | s |
| 23.75-24.01 | 3.74-3.70 | w-m |
| 24.75-24.93 | 3.59-3.57 | w-m |
| 25.01-25.47 | 3.56-3.49 | vs |
| 26.15-26.31 | 3.40-3.38 | w-m |
| 26.37-26.54 | 3.38-3.35 | m |
| 26.78-27.02 | 3.33-3.30 | w-m |
| 27.11-27.40 | 3.29-3.25 | m |

TABLE 1-continued

| 2-Theta | d(Å) | Intensity |
|---|---|---|
| 28.39-28.86 | 3.14-3.09 | w-m |
| 29.22-29.65 | 3.05-3.01 | m |
| 30.60-30.95 | 2.92-2.89 | w-m |
| 31.62-31.93 | 2.83-2.80 | w-m |
| 31.97-32.28 | 2.80-2.77 | w-s |
| 32.44-32.89 | 2.76-2.72 | w-m |
| 33.19-33.40 | 2.70-2.68 | vw-w |
| 33.51-33.82 | 2.67-2.65 | w-m |
| 34.72-35.08 | 2.58-2.55 | vw-w |

The AlPO78 material may be calcined in either air or nitrogen to remove the occluded template. In one embodiment of the invention, the AlPO78 is calcined at a temperature of at least 550° C. In another embodiment of the invention, the AlPO78 is calcined at a temperature of at least 600° C. The AlPO-78 is thermally stable upon calcination, and may be characterized by the x-ray diffraction pattern, having at least the d-spacings and relative intensities set forth in Table 2 below:

TABLE 2

| 2-Theta | d(Å) | Intensity |
|---|---|---|
| 8.02-8.12 | 11.01-10.88 | w |
| 8.40-8.51 | 10.51-10.38 | m |
| 8.63-8.73 | 10.23-10.12 | w-m |
| 9.78-9.89 | 9.03-8.93 | m-s |
| 10.70-10.81 | 8.26-8.17 | m-s |
| 12.83-12.95 | 6.89-6.82 | vw |
| 13.71-13.86 | 6.45-6.38 | vs |
| 14.00-14.13 | 6.32-6.26 | m-s |
| 16.16-16.64 | 5.48-5.32 | vw-w |
| 16.92-17.05 | 5.23-5.19 | vw-w |
| 17.44-17.56 | 5.08-5.04 | m |
| 17.79-17.93 | 4.98-4.94 | m-s |
| 19.68-19.89 | 4.51-4.46 | w |
| 20.43-20.61 | 4.34-4.30 | w-m |
| 21.17-21.35 | 4.19-4.16 | w-m |
| 21.81-21.99 | 4.07-4.04 | m-s |
| 22.15-22.53 | 4.01-3.94 | m-s |
| 22.55-22.74 | 3.94-3.91 | w-m |
| 23.95-24.25 | 3.71-3.67 | m-s |
| 24.57-24.79 | 3.62-3.59 | m-s |
| 25.87-26.31 | 3.44-3.38 | w-m |
| 26.49-26.71 | 3.36-3.33 | m |
| 27.40-27.88 | 3.25-3.20 | m-s |
| 28.32-28.52 | 3.15-3.13 | m-s |
| 28.85-29.02 | 3.09-3.07 | vw-w |
| 29.40-29.63 | 3.03-3.01 | w-m |
| 29.71-29.93 | 3.00-2.98 | vw |
| 30.28-30.44 | 2.95-2.93 | vw-w |
| 31.21-31.38 | 2.86-2.85 | vw-w |
| 32.18-32.50 | 2.79-2.75 | w-m |
| 32.65-32.92 | 2.74-2.72 | w-m |
| 33.00-33.15 | 2.71-2.70 | w-m |
| 34.25-34.41 | 2.61-2.60 | vw-w |
| 35.16-35.35 | 2.55-2.54 | w-m |

The stable calcined AlPO-78 material can be characterized on an anhydrous basis by the empirical formula:

$$H_w M_m^{2+} E P_x Si_y O_z$$

where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, H is a proton, "w" is the mole ratio of H to E and varies from 0 to 2.5, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, and "z" is the mole ratio of O to E and has a value determined by the equation:

$$z=(w+2\cdot m+3+5\cdot x+4\cdot y)/2$$

The crystalline AlPO-78 materials of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The AlPO78 compositions of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and syngas shift process. Specific reaction conditions and the types of feeds which can be used in these processes are set forth in U.S. Pat. Nos. 4,310,440, 4,440,871 and 5,126,308, which are incorporated by reference.

The AlPO-78 materials may also be used as a catalyst for the conversion of methanol to olefins. The methanol can be in the liquid or vapor phase with the vapor phase being preferred. Contacting the methanol with the AlPO-78 catalyst can be done in a continuous mode or a batch mode with a continuous mode being preferred. The amount of time that the methanol is in contact with the AlPO-78 catalyst must be sufficient to convert the methanol to the desired light olefin products. When the process is carried out in a batch process, the contact time varies from about 0.001 hrs to about 1 hr and preferably from about 0.01 hr to about 1.0 hr. The longer contact times are used at lower temperatures while shorter times are used at higher temperatures. When the process is carried out in a continuous mode, the Weight Hourly Space Velocity (WHSV) based on methanol can vary from about 1 hr-1 to about 1000 hr-1 and preferably from about 1 hr-1 to about 100 hr-1.

Generally, the process must be carried out at elevated temperatures in order to form light olefins at a fast enough rate. Thus, the process should be carried out at a temperature of about 300° C. to about 600° C., preferably from about 400° C. to about 550° C. and most preferably from about 435° C. to about 525° C. The process may be carried out over a wide range of pressure including autogenous pressure. Thus, the pressure can vary from about 0 kPa (0 psig) to about 1724 kPa (250 psig) and preferably from about 34 kPa (5 psig) to about 345 kPa (50 psig).

Optionally, the methanol feedstock may be diluted with an inert diluent in order to more efficiently convert the methanol to olefins. Examples of the diluents which may be used are helium, argon, nitrogen, carbon monoxide, carbon dioxide, hydrogen, steam, paraffinic hydrocarbons, e. g., methane, aromatic hydrocarbons, e. g., benzene, toluene and mixtures thereof. The amount of diluent used can vary considerably and is usually from about 5 to about 90 mole percent of the feedstock and preferably from about 25 to about 75 mole percent.

The actual configuration of the reaction zone may be any well known catalyst reaction apparatus known in the art. Thus, a single reaction zone or a number of zones arranged in series or parallel may be used. In such reaction zones the methanol feedstock is flowed through a bed containing the AlPO-78 catalyst. When multiple reaction zones are used, one or more AlPO-78 catalysts may be used in series to produce the desired product mixture. Instead of a fixed bed, a dynamic bed system, (e. g., fluidized bed or moving bed), may be used. Such a dynamic system would facilitate any regeneration of the AlPO-78 catalyst that may be required. If regeneration is required, the AlPO-78 catalyst can be continuously introduced as a moving bed to a regeneration zone where it can be regenerated by means such as oxidation in an oxygen containing atmosphere to remove carbonaceous materials.

The AlPO-78 materials of this invention can also be used as an adsorbent for water vapor. The adsorbent may be a component of an adsorption heat pump apparatus. Adsorbents used for adsorption heat pump purposes are desired to have a high capacity for water vapor, as well as a large crystallographic density. The crystallographic density of microporous crystalline materials is conveniently expressed in units of T-atom/1000 $Å^3$. Generally speaking, adsorbents with a low density can be problematic since they would require a large volume of material to take up a given quantity of adsorbate. This can be troublesome if space is limited in the application. It is thus of interest to consider uptake capacity on a volumetric basis as opposed to a gravimetric basis.

As measured, AlPO-78 has superior uptake characteristics (on a volumetric basis) to both SAPO-34 and SAPO-5, which are preferred silicoaluminophosphate materials for use in adsorption heat pumps (see U.S. Pat. Nos. 7,422,993 and 9,517,942). Thus, AlPO-78 could be a preferred material for use in adsorption heat pumps.

The following examples are presented in illustration of this invention and are not intended as undue limitations on the generally broad scope of the invention as set out in the appended claims. The products will be designated with names that contain the suffix "-78" to indicate the "-78" structure and prefix that reflects the compositional nature of the product, such as "SAPO" for a silicoaluminophosphate, "ZnAPO" for a zinc aluminophosphate, and "MgAPSO" for a magnesium silicoaluminophosphate, etc.

The structure of the AlPO-78 compositions of this invention was determined by x-ray analysis. The x-ray patterns presented in the following examples were obtained using standard x-ray powder diffraction techniques. The radiation source was a high-intensity, x-ray tube operated at 45 kV and 35 mA. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art, the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, w, and vw which represent very strong, strong, medium, weak, and very weak respectively. In terms of $100 \times I/I_o$, the above designations are defined as:

vw=0-5; w=5-15; m=15-40: s=40-75 and vs=75-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

EXAMPLE 1

117.03 g of water was weighed into a 500 cc Teflon bottle. 65.43 g of 1,4-dibromobutane (99%) was added, and then the mixture was placed into an ice bath. To the above mixture, 51.6 g of Piperidine (99%) was added under magnetic stirring. The water and piperidine combined to form a cloudy phase while the denser 1,4-dibromobutane remained on the bottom. The Teflon bottle was placed under an overheard mixer and stirred somewhat vigorously. After about 5 minutes a clear light yellow template solution is formed. The reaction is continued for about 1 hour before the stirring is stopped.

EXAMPLE 2

1154 g of the solution from Example 1 was contacted with 355.1 g of Ag$_2$O in a round-bottom flask, which combined to form a grey opaque solution. The flask was placed under a high speed overheard stirrer for stirring at room temperature for 1 day. The sample was filtered to remove the precipitated silver bromide and the final solution was sent for water analysis, which showed that the sample was composed of 78.6% water.

EXAMPLE 3

51.85g of the product of Example 2 was combined with 4.56 g of Al(OH)$_3$ (Al=27.9%). 0.48 g of Ludox AS-40 (Sigma-Aldrich) was added to the gel followed by 11.77 g phosphoric acid, 85%, which is added very slowly due to the resulting exotherm. The gel was then stirred vigorously for 2 hours. The final gel mixture was distributed equally into 2 45 cc autoclaves and digested for 4 and 5 days at 170° C. Afterwards, the gels were cooled to room temperature, the products were isolated by centrifugation, and the solids dried at 100° C. overnight. XRD analysis of the as-synthesized material revealed the following lines:

| 2-Theta | d(Å) | Intensity |
|---|---|---|
| 7.96 | 11.09 | m |
| 8.31 | 10.63 | m |
| 8.87 | 9.97 | s |
| 9.82 | 9.00 | vs |
| 10.76 | 8.21 | m |
| 11.80 | 7.49 | m |
| 13.57 | 6.52 | s |
| 14.16 | 6.25 | vs |
| 15.93 | 5.56 | m |
| 16.23 | 5.46 | s |
| 16.75 | 5.29 | m |
| 17.34 | 5.11 | s |
| 17.87 | 4.96 | s |
| 18.12 | 4.89 | s |
| 18.82 | 4.71 | w |
| 19.62 | 4.52 | w |
| 20.86 | 4.26 | s |
| 21.60 | 4.11 | m |
| 22.00 | 4.04 | s |
| 22.26 | 3.99 | s |
| 22.67 | 3.92 | m |
| 23.23 | 3.83 | w |
| 23.63 | 3.76 | s |
| 23.93 | 3.72 | w |
| 25.15 | 3.54 | vs |
| 26.25 | 3.39 | m |
| 26.49 | 3.36 | m |
| 26.94 | 3.31 | m |
| 27.26 | 3.27 | m |
| 28.54 | 3.13 | m |
| 29.54 | 3.02 | m |
| 30.99 | 2.88 | w |
| 31.73 | 2.82 | m |
| 32.11 | 2.79 | m |
| 32.55 | 2.75 | w |
| 33.33 | 2.69 | vw |
| 33.77 | 2.65 | w |
| 35.02 | 2.56 | vw |

The products of these syntheses were identified as SAPO-78 by XRD. Elemental analysis gave an observed stoichiometry of Si$_{0.055}$AlP$_{0.992}$.

EXAMPLE 4

The product of Example 3 was calcined in air at 600° C. in a muffle furnace. The furnace was ramped at 2° C./min to the target temperature. After calcination for 4 hours at 600° C., the sample was cooled to room temperature. XRD analysis of the calcined material revealed the following lines:

| 2-Theta | d(Å) | Intensity |
|---|---|---|
| 8.09 | 10.93 | w |
| 8.47 | 10.44 | m |
| 8.69 | 10.17 | m |
| 9.84 | 8.98 | s |
| 10.76 | 8.21 | s |
| 12.90 | 6.86 | vw |
| 13.81 | 6.41 | vs |
| 14.08 | 6.29 | m |
| 16.22 | 5.46 | vw |
| 16.57 | 5.35 | w |
| 16.99 | 5.22 | vw |
| 17.55 | 5.06 | m |
| 17.87 | 4.96 | s |
| 19.76 | 4.49 | w |
| 20.54 | 4.32 | w |
| 21.22 | 4.18 | w |
| 21.92 | 4.05 | m |
| 22.39 | 3.97 | m |
| 22.64 | 3.92 | w |
| 24.03 | 3.70 | m |
| 24.21 | 3.67 | m |
| 24.69 | 3.60 | s |
| 25.97 | 3.43 | w |
| 26.27 | 3.39 | m |
| 26.61 | 3.35 | m |
| 27.46 | 3.25 | m |
| 27.82 | 3.20 | m |
| 28.40 | 3.14 | m |
| 28.96 | 3.08 | w |
| 29.54 | 3.02 | w |

| 2-Theta | d(Å) | Intensity |
|---|---|---|
| 29.89 | 2.99 | vw |
| 30.38 | 2.94 | vw |
| 31.31 | 2.85 | w |
| 31.69 | 2.82 | w |
| 32.34 | 2.77 | w |
| 32.77 | 2.73 | w |
| 33.09 | 2.71 | m |
| 34.35 | 2.61 | vw |
| 35.30 | 2.54 | m |

The surface area of the calcined SAPO-78 (measured by nitrogen adsorption at 77 K) was determined to be 394 m$^2$/g, and the micropore volume was determined to be 0.20 cm$^3$/g.

EXAMPLE 5

134.54 g of the product of Example 2 was combined with 10.94 g of Al(OH)$_3$ (Al=27.9%). 11.77 g phosphoric acid, 85%, which is added very slowly due to resulting exotherm, is stirred in. The gel was then mixed vigorously for 2 hours. The final gel was transferred to a 300 cc stirred autoclave and digested for 5 days at 170° C. at 250 rpm. Afterwards, the gel was cooled to room temperature, the product was isolated by centrifugation, and the solids dried at 100° C. overnight. XRD analysis of the as-synthesized material revealed the following lines:

| 2-Theta | d(Å) | Intensity |
|---|---|---|
| 7.91 | 11.17 | m |
| 8.23 | 10.74 | s |
| 8.98 | 9.84 | s |
| 9.77 | 9.05 | vs |
| 10.64 | 8.31 | m |
| 10.97 | 8.06 | m |
| 13.34 | 6.63 | s |
| 13.50 | 6.56 | s |
| 14.18 | 6.24 | s |
| 14.49 | 6.11 | s |
| 15.59 | 5.68 | m |
| 15.83 | 5.59 | m |
| 16.09 | 5.50 | s |
| 16.63 | 5.32 | m |
| 16.95 | 5.23 | m |
| 17.29 | 5.13 | s |
| 17.99 | 4.93 | s |
| 18.43 | 4.81 | s |
| 19.13 | 4.64 | w |
| 19.76 | 4.49 | m |
| 20.74 | 4.28 | s |
| 21.12 | 4.20 | m |
| 21.72 | 4.09 | m |
| 21.95 | 4.05 | s |
| 22.69 | 3.92 | m |
| 23.39 | 3.80 | m |
| 23.65 | 3.76 | s |
| 23.83 | 3.73 | m |
| 24.82 | 3.58 | w |
| 25.21 | 3.53 | vs |
| 26.23 | 3.40 | m |
| 26.43 | 3.37 | m |
| 26.89 | 3.31 | m |
| 27.18 | 3.28 | m |
| 28.42 | 3.14 | w |
| 28.80 | 3.10 | w |
| 29.32 | 3.04 | m |
| 30.71 | 2.91 | w |
| 31.25 | 2.86 | m |
| 31.99 | 2.80 | s |
| 32.25 | 2.77 | m |
| 32.81 | 2.73 | m |
| 33.25 | 2.69 | w |
| 33.61 | 2.66 | vw |
| 34.92 | 2.57 | vw |
| 35.21 | 2.55 | w |

The product of this synthesis was identified as AlPO-78 by XRD. Elemental analysis gave stoichiometry of AlP$_{0.992}$.

EXAMPLE 6

The product of Example 5 was calcined in air at 600° C. in a muffle furnace. The furnace was ramped at 2° C./min to the target temperature. After calcination for 4 hours at 600° C., the sample was cooled to room temperature. The surface area of the calcined AlPO-78 (measured by nitrogen adsorption at 77 K) was determined to be 392 m$^2$/g, and the micropore volume was determined to be 0.22 cm$^3$/g. XRD analysis of the calcined material revealed the following lines:

| 2-Theta | d(Å) | Intensity |
|---|---|---|
| 8.05 | 10.97 | w |
| 8.44 | 10.46 | m |
| 8.68 | 10.18 | m |
| 9.82 | 9.00 | s |
| 10.74 | 8.23 | m |
| 12.89 | 6.86 | vw |
| 13.76 | 6.43 | vs |
| 14.05 | 6.30 | m |
| 16.20 | 5.47 | vw |
| 16.96 | 5.22 | w |
| 17.49 | 5.07 | m |
| 17.84 | 4.97 | m |
| 19.74 | 4.49 | w |
| 20.48 | 4.33 | w |
| 21.30 | 4.17 | w |
| 21.89 | 4.06 | s |
| 22.30 | 3.98 | s |
| 22.59 | 3.93 | w |
| 24.01 | 3.70 | m |
| 24.67 | 3.61 | m |
| 25.96 | 3.44 | w |
| 26.55 | 3.36 | m |
| 27.76 | 3.21 | m |
| 28.46 | 3.13 | m |
| 29.52 | 3.02 | w |
| 31.29 | 2.86 | vw |
| 31.61 | 2.83 | w |
| 32.33 | 2.77 | w |
| 32.87 | 2.72 | w |
| 35.23 | 2.55 | w |

McBain adsorption experiments revealed the following uptake behavior:

| Molecule | Pressure (torr) | Wt. % Uptake |
|---|---|---|
| H$_2$O | 4.6 | 25.7 |
| CO$_2$ | 250 | 3.5 |
| n-C$_4$H$_{10}$ | 700 | 0.4 |

EXAMPLE 7

115.3 g of the product of Example 2 was combined with 11.15 g of alumina trihydrate (Al=34.3%), 1.05 g Ludox AS-40, and 25.83 g phosphoric acid, 85%, which is added very slowly due to resulting exotherm, is stirred in. The gel was then mixed vigorously for 2 hours. The final gel was transferred to a 300cc stirred autoclave and digested for 1 day at 100° then 3 days at 160° C. at 150 rpm. Afterwards, the gel was cooled to room temperature, the product was isolated by centrifugation, and the solids dried at 100° C. overnight. The product of this synthesis was identified as SAPO-78 by XRD. Elemental analysis gave a stoichiometry of $Si_{0.056}AlP_{0.860}$.

EXAMPLE 8

The product of Example 7 was calcined in air at 600° C. in a muffle furnace. The furnace was ramped at 2° C./min to the target temperature. After calcination for 4 hours at 600° C., the sample was cooled to room temperature. The surface area of the calcined SAPO-78 (measured by nitrogen adsorption at 77 K) was determined to be 417 $m^2/g$, and the micropore volume was determined to be 0.21 $cm^3/g$.

COMPARATIVE EXAMPLE 1

SAPO-34 was synthesized following Example 35 of U.S. Pat. No. 4,440,871, incorporated herein by reference. After the as-synthesized SAPO-34 was isolated from the mother liquor and dried, it was calcined at 600° C. for 4 hours in air. XRD analysis of the calcined material showed that the product was pure SAPO-34.

COMPARATIVE EXAMPLE 2

SAPO-5 was synthesized following Example 12 of U.S. Pat. No. 4,440,871, incorporated by reference. After the as-synthesized SAPO-5 was isolated from the mother liquor and dried, it was calcined at 600° C. for 4 hours in air. XRD analysis of the calcined material showed that the product was pure SAPO-5.

EXAMPLE 9

Figure 2:
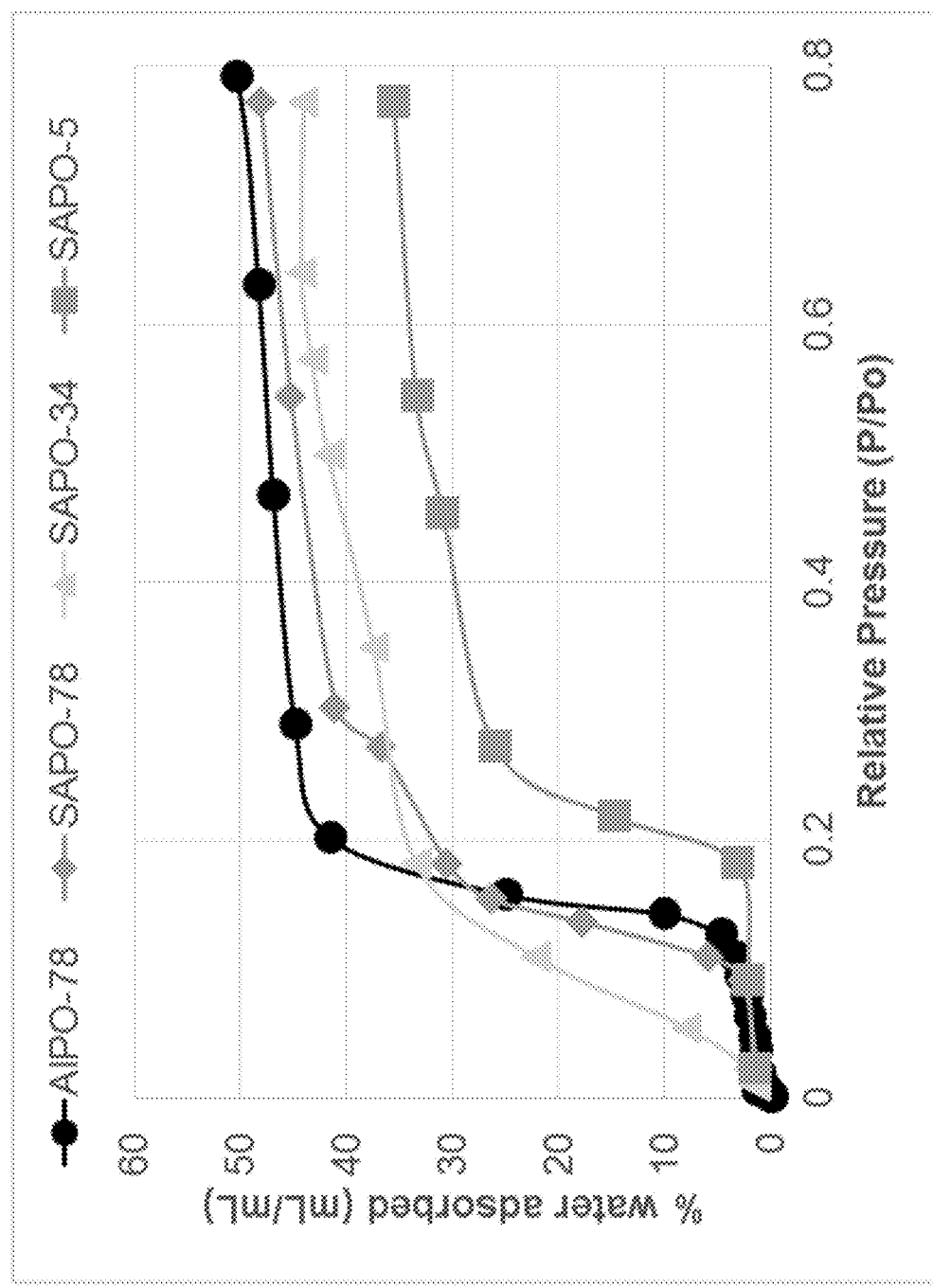
FIG. 2 is a graph showing water adsorption isotherms of exemplary AlPO-78 materials along with comparative example materials. Details are discussed in Example 9.
Figure 3:
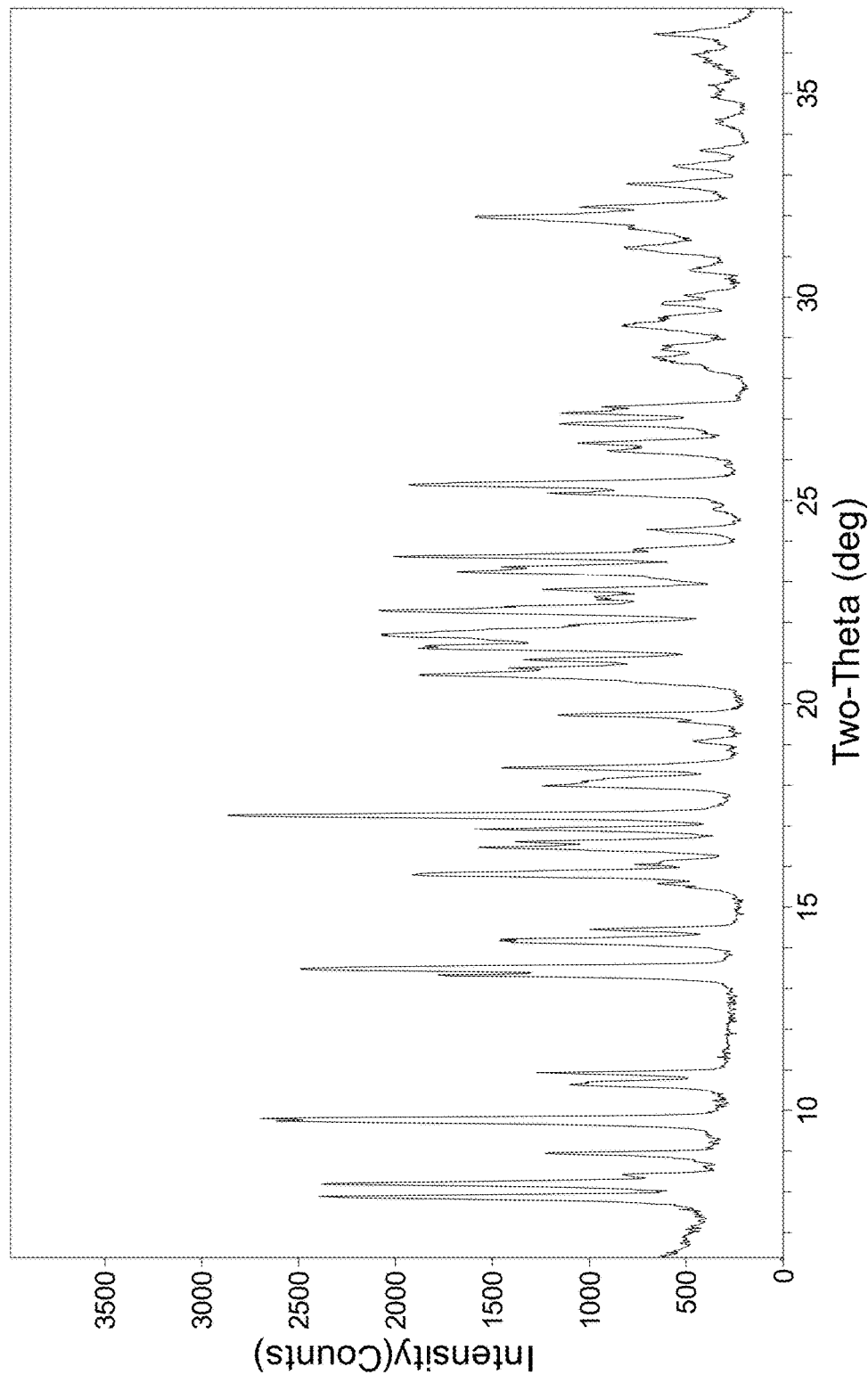
FIG. 3 is an x-ray diffraction pattern of an exemplary AlPO-78 material in the as-synthesized form.
Figure 4:
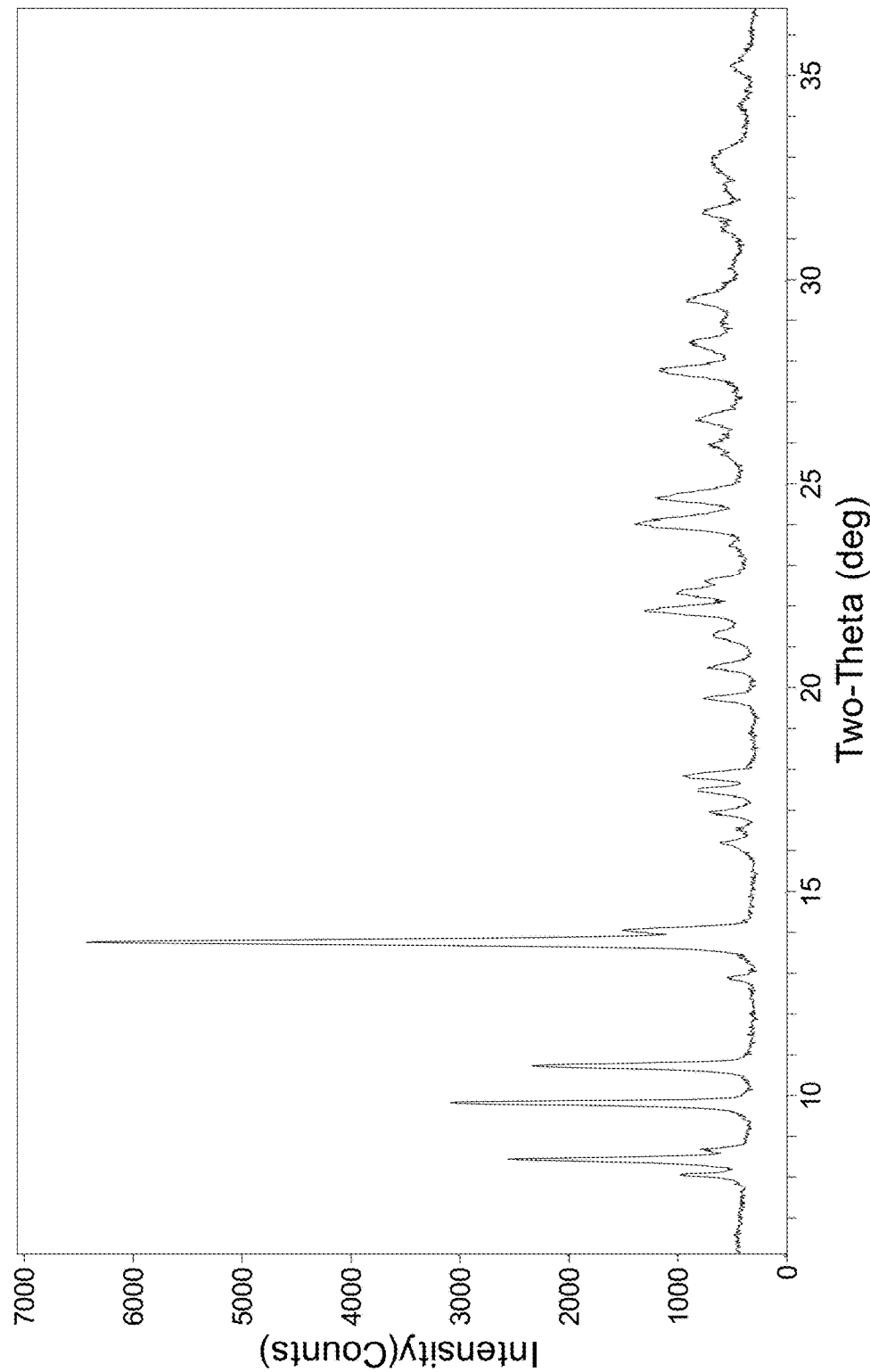
FIG. 4 is an x-ray diffraction pattern of an exemplary AlPO-78 material in the calcined form.

The products of Example 6, Example 8, Comparative Example 1, and Comparative Example 2 were tested for water vapor adsorption in a McBain gravimetric balance. Prior to water vapor adsorption, the materials heated at 400° C. under vacuum. Water adsorption isotherms were recorded for each material at 25° C., and are displayed in FIG. 2. Saturation capacities were measured in terms of mass %, then converted to volume % using the crystal density of each framework, which is determined from the unit cell of each material. The results are displayed in Table 9:

| Material | Saturation Capacity (mass %) | Crystal Density (g/mL) | Volumetric Capacity (volume %) |
|---|---|---|---|
| AlPO-78 | 29.7 | 1.70 | 50.5 |
| SAPO-78 | 28.3 | 1.70 | 48.1 |
| SAPO-34 | 31.0 | 1.43 | 44.3 |
| SAPO-5 | 20.3 | 1.75 | 35.6 |

It is seen that both AlPO-78 and SAPO-78 have superior volumetric capacity for water vapor over the comparative examples SAPO-34 and SAPO-5.

Specific Embodiments

While the following is described in conjunction with specific embodiments, it will be understood that this description is intended to illustrate and not limit the scope of the preceding description and the appended claims.

A first embodiment of the invention is a microporous crystalline material that has an empirical composition in an as-synthesized form and on an anhydrous basis expressed by an empirical formula $R^+_r M_m^{2+} E P_x Si_y O_z$ where M is at least one framework divalent cation and is selected from the group consisting of alkaline earth and transition metals, wherein M is a cation selected from the group consisting of beryllium, magnesium, cobalt (II), manganese, zinc, iron (II), nickel and mixtures thereof. R is an organoammonium cation, "r" is the mole ratio of R to E and varies from about 0.1 to about 2.0, "m" is the mole ratio of M to E and varies from 0 to about 1.0, "x" is a mole ratio of P to E and varies from 0.5 to about 2.0, a ratio of silicon to E is represented by "y" which varies from about 0 to about 1.0, E is a trivalent element which is tetrahedrally coordinated, is present in the framework, and is selected from the group consisting of aluminum, gallium, iron (III) and boron and "z" is a mole ratio of O to E and is given by an equation $z=(2 \cdot m+r+3+5 \cdot x+4 \cdot y)/2$ and is characterized by a following x-ray diffraction pattern, having at least the d-spacings and relative intensities set forth in Table 1.

TABLE 1

| 2-Theta | d(Å) | Intensity |
|---|---|---|
| 7.88-7.98 | 11.21-11.07 | m-s |
| 8.15-8.50 | 10.84-10.39 | m-s |
| 8.82-9.05 | 10.01-9.76 | s |
| 9.67-9.96 | 9.14-8.87 | s-vs |
| 10.58-10.81 | 8.35-8.17 | m |
| 10.92-11.71 | 8.09-7.55 | m-s |
| 13.21-13.67 | 6.69-6.47 | s |
| 14.10-14.54 | 6.27-6.08 | s-vs |
| 15.48-16.02 | 5.72-5.53 | m |
| 16.05-16.24 | 5.52-5.45 | s |
| 16.44-16.81 | 5.39-5.28 | m |
| 16.87-17.01 | 5.25-5.21 | m-s |
| 17.19-17.43 | 5.15-5.08 | s |
| 17.78-18.46 | 4.98-4.80 | s-vs |
| 18.73-19.22 | 4.73-4.61 | vw-w |
| 19.48-19.86 | 4.55-4.47 | w-m |
| 20.47-20.96 | 4.33-4.23 | s |
| 21.00-21.45 | 4.23-4.14 | m-s |
| 21.52-21.73 | 4.12-4.08 | m-s |
| 21.88-22.10 | 4.06-4.02 | s |
| 22.15-22.42 | 4.01-3.96 | m-s |
| 22.52-22.95 | 3.94-3.87 | w-m |
| 23.14-23.52 | 3.84-3.78 | w-m |
| 23.58-23.71 | 3.77-3.75 | s |
| 23.75-24.01 | 3.74-3.70 | w-m |
| 24.75-24.93 | 3.59-3.57 | w-m |
| 25.01-25.47 | 3.56-3.49 | vs |
| 26.15-26.31 | 3.40-3.38 | w-m |
| 26.37-26.54 | 3.38-3.35 | m |
| 26.78-27.02 | 3.33-3.30 | w-m |
| 27.11-27.40 | 3.29-3.25 | m |
| 28.39-28.86 | 3.14-3.09 | w-m |
| 29.22-29.65 | 3.05-3.01 | m |
| 30.60-30.95 | 2.92-2.89 | w-m |
| 31.62-31.93 | 2.83-2.80 | w-m |
| 31.97-32.28 | 2.80-2.77 | w-s |
| 32.44-32.89 | 2.76-2.72 | w-m |
| 33.19-33.40 | 2.70-2.68 | vw-w |
| 33.51-33.82 | 2.67-2.65 | w-m |
| 34.72-35.08 | 2.58-2.55 | vw-w |

An embodiment of the invention is one, any or all of prior embodiments in this paragraph up through the first embodiment in this paragraph wherein after being calcined, the AlPO-78 material is characterized by the x-ray diffraction pattern, having at least the d-spacings and relative intensities set forth in Table 2 below.

TABLE 2

| 2-Theta | d(Å) | Intensity |
|---|---|---|
| 8.02-8.12 | 11.01-10.88 | w |
| 8.40-8.51 | 10.51-10.38 | m |
| 8.63-8.73 | 10.23-10.12 | w-m |
| 9.78-9.89 | 9.03-8.93 | m-s |
| 10.70-10.81 | 8.26-8.17 | m-s |
| 12.83-12.95 | 6.89-6.82 | vw |
| 13.71-13.86 | 6.45-6.38 | vs |
| 14.00-14.13 | 6.32-6.26 | m-s |
| 16.16-16.64 | 5.48-5.32 | vw-w |
| 16.92-17.05 | 5.23-5.19 | vw-w |
| 17.44-17.56 | 5.08-5.04 | m |
| 17.79-17.93 | 4.98-4.94 | m-s |
| 19.68-19.89 | 4.51-4.46 | w |
| 20.43-20.61 | 4.34-4.30 | w-m |
| 21.17-21.35 | 4.19-4.16 | w-m |
| 21.81-21.99 | 4.07-4.04 | m-s |
| 22.15-22.53 | 4.01-3.94 | m-s |
| 22.55-22.74 | 3.94-3.91 | w-m |
| 23.95-24.25 | 3.71-3.67 | m-s |
| 24.57-24.79 | 3.62-3.59 | m-s |
| 25.87-26.31 | 3.44-3.38 | w-m |
| 26.49-26.71 | 3.36-3.33 | m |
| 27.40-27.88 | 3.25-3.20 | m-s |
| 28.32-28.52 | 3.15-3.13 | m-s |
| 28.85-29.02 | 3.09-3.07 | vw-w |
| 29.40-29.63 | 3.03-3.01 | w-m |
| 29.71-29.93 | 3.00-2.98 | vw |
| 30.28-30.44 | 2.95-2.93 | vw-w |
| 31.21-31.38 | 2.86-2.85 | vw-w |
| 32.18-32.50 | 2.79-2.75 | w-m |
| 32.65-32.92 | 2.74-2.72 | w-m |
| 33.00-33.15 | 2.71-2.70 | w-m |
| 34.25-34.41 | 2.61-2.60 | vw-w |
| 35.16-35.35 | 2.55-2.54 | w-m |

An embodiment of the invention is one, any or all of prior embodiments in this paragraph up through the first embodiment in this paragraph wherein the microporous crystalline material is characterized on an anhydrous basis by the empirical formula $H_w M_m^{2+} E P_x Si_y O_z$ where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, H is a proton, w" is the mole ratio of H to E and varies from 0 to 2.5, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0.05 to about 1.0, "m"+"y"≥0.1, and "z" is the mole ratio of O to E and has a value determined by the equation $z=(w+2 \cdot m+3+5 \cdot x+4 \cdot y)/2$. An embodiment of the invention is one, any or all of prior embodiments in this paragraph up through the first embodiment in this paragraph wherein the microporous crystalline material indexes on a unit cell with hexagonal axes with lattice parameters a=12.768 Å and c=60.825 Å and has an ABC-6 net structure with the stacking sequence repeating every 24 layers along the c-axis (p=60.825/2.5=24.33).

A second embodiment of the invention is a method of making a AlPO-78 microporous crystalline material comprising preparing a reaction mixture containing reactive sources described in terms of molar ratios of the oxides by a formula $aR_2O\ bMO\ E_2O_3\ cP_2O_5\ dSiO_2\ eH_2O$ where "a" varies from about 0.75 to about 16, "b" varies from about 0 to about 2, "c" varies from about 0.8 to about 8, "d" varies from about 0 to about 4, and "e" varies from 30 to 800 wherein reactive sources of R, E, phosphorus and one or both M and silicon; reacting the reaction mixture at a temperature from about 60° C. to about 200° C. for a period of about 1 day to about 21 days; and isolating a solid product from a heterogeneous mixture wherein the AlPO-78 microporous material, is characterized by the x-ray following diffraction pattern, having at least the d-spacings and relative intensities set forth in Table 1.

TABLE 1

| 2-Theta | d(Å) | Intensity |
|---|---|---|
| 7.88-7.98 | 11.21-11.07 | m-s |
| 8.15-8.50 | 10.84-10.39 | m-s |
| 8.82-9.05 | 10.01-9.76 | s |
| 9.67-9.96 | 9.14-8.87 | s-vs |
| 10.58-10.81 | 8.35-8.17 | m |
| 10.92-11.71 | 8.09-7.55 | m-s |
| 13.21-13.67 | 6.69-6.47 | s |
| 14.10-14.54 | 6.27-6.08 | s-vs |
| 15.48-16.02 | 5.72-5.53 | m |
| 16.05-16.24 | 5.52-5.45 | s |
| 16.44-16.81 | 5.39-5.28 | m |
| 16.87-17.01 | 5.25-5.21 | m-s |
| 17.19-17.43 | 5.15-5.08 | s |
| 17.78-18.46 | 4.98-4.80 | s-vs |
| 18.73-19.22 | 4.73-4.61 | vw-w |
| 19.48-19.86 | 4.55-4.47 | w-m |
| 20.47-20.96 | 4.33-4.23 | s |
| 21.00-21.45 | 4.23-4.14 | m-s |
| 21.52-21.73 | 4.12-4.08 | m-s |
| 21.88-22.10 | 4.06-4.02 | s |
| 22.15-22.42 | 4.01-3.96 | m-s |
| 22.52-22.95 | 3.94-3.87 | w-m |
| 23.14-23.52 | 3.84-3.78 | w-m |
| 23.58-23.71 | 3.77-3.75 | s |
| 23.75-24.01 | 3.74-3.70 | w-m |
| 24.75-24.93 | 3.59-3.57 | w-m |
| 25.01-25.47 | 3.56-3.49 | vs |
| 26.15-26.31 | 3.40-3.38 | w-m |
| 26.37-26.54 | 3.38-3.35 | m |
| 26.78-27.02 | 3.33-3.30 | w-m |
| 27.11-27.40 | 3.29-3.25 | m |
| 28.39-28.86 | 3.14-3.09 | w-m |
| 29.22-29.65 | 3.05-3.01 | m |
| 30.60-30.95 | 2.92-2.89 | w-m |
| 31.62-31.93 | 2.83-2.80 | w-m |
| 31.97-32.28 | 2.80-2.77 | w-s |
| 32.44-32.89 | 2.76-2.72 | w-m |
| 33.19-33.40 | 2.70-2.68 | vw-w |
| 33.51-33.82 | 2.67-2.65 | w-m |
| 34.72-35.08 | 2.58-2.55 | vw-w |

An embodiment of the invention is one, any or all of prior embodiments in this paragraph up through the first embodiment in this paragraph wherein the AlPO-78 is calcined at a temperature of at least 550° C. and is characterized by the x-ray diffraction pattern, having at least the d-spacings and relative intensities set forth in Table 2 below.

TABLE 2

| 2-Theta | d(Å) | Intensity |
|---|---|---|
| 8.02-8.12 | 11.01-10.88 | w |
| 8.40-8.51 | 10.51-10.38 | m |
| 8.63-8.73 | 10.23-10.12 | w-m |
| 9.78-9.89 | 9.03-8.93 | m-s |
| 10.70-10.81 | 8.26-8.17 | m-s |
| 12.83-12.95 | 6.89-6.82 | vw |
| 13.71-13.86 | 6.45-6.38 | vs |
| 14.00-14.13 | 6.32-6.26 | m-s |
| 16.16-16.64 | 5.48-5.32 | vw-w |
| 16.92-17.05 | 5.23-5.19 | vw-w |
| 17.44-17.56 | 5.08-5.04 | m |
| 17.79-17.93 | 4.98-4.94 | m-s |
| 19.68-19.89 | 4.51-4.46 | w |
| 20.43-20.61 | 4.34-4.30 | w-m |
| 21.17-21.35 | 4.19-4.16 | w-m |
| 21.81-21.99 | 4.07-4.04 | m-s |

TABLE 2-continued

| 2-Theta | d(Å) | Intensity |
|---|---|---|
| 22.15-22.53 | 4.01-3.94 | m-s |
| 22.55-22.74 | 3.94-3.91 | w-m |
| 23.95-24.25 | 3.71-3.67 | m-s |
| 24.57-24.79 | 3.62-3.59 | m-s |
| 25.87-26.31 | 3.44-3.38 | w-m |
| 26.49-26.71 | 3.36-3.33 | m |
| 27.40-27.88 | 3.25-3.20 | m-s |
| 28.32-28.52 | 3.15-3.13 | m-s |
| 28.85-29.02 | 3.09-3.07 | vw-w |
| 29.40-29.63 | 3.03-3.01 | w-m |
| 29.71-29.93 | 3.00-2.98 | vw |
| 30.28-30.44 | 2.95-2.93 | vw-w |
| 31.21-31.38 | 2.86-2.85 | vw-w |
| 32.18-32.50 | 2.79-2.75 | w-m |
| 32.65-32.92 | 2.74-2.72 | w-m |
| 33.00-33.15 | 2.71-2.70 | w-m |
| 34.25-34.41 | 2.61-2.60 | vw-w |
| 35.16-35.35 | 2.55-2.54 | w-m |

An embodiment of the invention is one, any or all prior embodiments in this paragraph up through the first embodiment in this paragraph wherein the sources of aluminum are selected from the group consisting of aluminum alkoxides, precipitated aluminas, aluminum metal, aluminum hydroxide, aluminum salts and alumina sols. An embodiment of the invention is one, any or all prior embodiments in this paragraph up through the first embodiment in this paragraph wherein sources of phosphorus are selected from the group consisting of orthophosphoric acid, phosphorus pentoxide, and ammonium dihydrogen phosphate. An embodiment of the invention is one, any or all of prior embodiments in this paragraph up through the first embodiment in this paragraph wherein sources of silica are selected from the group consisting of tetraethylorthosilicate, colloidal silica, and precipitated silica. An embodiment of the invention is one, any or all prior embodiments in this paragraph up through the first embodiment in this paragraph wherein sources of E elements are selected from the group consisting of organoammonium borates, boric acid, precipitated gallium oxyhydroxide, gallium sulfate, ferric sulfate, and ferric chloride. An embodiment of the invention is one, any or all prior embodiments in this paragraph up through the first embodiment in this paragraph wherein sources of the M metals are selected from the group consisting of halide salts, nitrate salts, acetate salts, and sulfate salts of the respective alkaline earth and transition metals. An embodiment of the invention is one, any or all of prior embodiments in this paragraph up through the first embodiment in this paragraph wherein R is an organoammonium cation prepared from a reaction of an aqueous mixture of a cyclic secondary amine and an organic dihalide. An embodiment of the invention is one, any or all prior embodiments in this paragraph up through the first embodiment in this paragraph wherein the cyclic secondary amines are selected from the group consisting of piperidine, homopiperidine, pyrrolidine, and morpholine. An embodiment of the invention is one, any or all prior embodiments in this paragraph up through the first embodiment in this paragraph wherein the AlPO-78 microporous crystalline material is calcined at a temperature of at least 600° C.

A third embodiment of the invention is a process of separating mixtures of molecular species, removing contaminants or catalyzing hydrocarbon conversion processes comprising contacting a feed stream with a microporous crystalline material that has an empirical composition in a calcined form and on an anhydrous basis expressed by an empirical formula $R^-_rM_m^{2+}EP_xSi_yO_z$ where M is at least one framework divalent cation and is selected from the group consisting of alkaline earth and transition metals, wherein M is a cation selected from the group consisting of beryllium, magnesium, cobalt (II), manganese, zinc, iron (II), nickel and mixtures thereof. R is an organoammonium cation, "r" is the mole ratio of R to E and varies from about 0.1 to about 2.0, "m" is the mole ratio of M to E and varies from 0 to about 1.0, "x" is a mole ratio of P to E and varies from 0.5 to about 2.0, a ratio of silicon to E is represented by "y" which varies from about 0 to about 1.0, E is a trivalent element which is tetrahedrally coordinated, is present in the framework, and is selected from the group consisting of aluminum, gallium, iron (III) and boron and "z" is a mole ratio of O to E and is given by an equation $z=(2 \cdot m+r+3+5 \cdot x+4y)/2$ and is characterized by an x-ray following diffraction pattern, having at least the d-spacings and relative intensities set forth in Table 2.

TABLE 2

| 2-Theta | d(Å) | Intensity |
|---|---|---|
| 8.02-8.12 | 11.01-10.88 | w |
| 8.40-8.51 | 10.51-10.38 | m |
| 8.63-8.73 | 10.23-10.12 | w-m |
| 9.78-9.89 | 9.03-8.93 | m-s |
| 10.70-10.81 | 8.26-8.17 | m-s |
| 12.83-12.95 | 6.89-6.82 | vw |
| 13.71-13.86 | 6.45-6.38 | vs |
| 14.00-14.13 | 6.32-6.26 | m-s |
| 16.16-16.64 | 5.48-5.32 | vw-w |
| 16.92-17.05 | 5.23-5.19 | vw-w |
| 17.44-17.56 | 5.08-5.04 | m |
| 17.79-17.93 | 4.98-4.94 | m-s |
| 19.68-19.89 | 4.51-4.46 | w |
| 20.43-20.61 | 4.34-4.30 | w-m |
| 21.17-21.35 | 4.19-4.16 | w-m |
| 21.81-21.99 | 4.07-4.04 | m-s |
| 22.15-22.53 | 4.01-3.94 | m-s |
| 22.55-22.74 | 3.94-3.91 | w-m |
| 23.95-24.25 | 3.71-3.67 | m-s |
| 24.57-24.79 | 3.62-3.59 | m-s |
| 25.87-26.31 | 3.44-3.38 | w-m |
| 26.49-26.71 | 3.36-3.33 | m |
| 27.40-27.88 | 3.25-3.20 | m-s |
| 28.32-28.52 | 3.15-3.13 | m-s |
| 28.85-29.02 | 3.09-3.07 | vw-w |
| 29.40-29.63 | 3.03-3.01 | w-m |
| 29.71-29.93 | 3.00-2.98 | vw |
| 30.28-30.44 | 2.95-2.93 | vw-w |
| 31.21-31.38 | 2.86-2.85 | vw-w |
| 32.18-32.50 | 2.79-2.75 | w-m |
| 32.65-32.92 | 2.74-2.72 | w-m |
| 33.00-33.15 | 2.71-2.70 | w-m |
| 34.25-34.41 | 2.61-2.60 | vw-w |
| 35.16-35.35 | 2.55-2.54 | w-m |

An embodiment of the invention is one, any or all of prior embodiments in this paragraph up through the second embodiment in this paragraph wherein the separation of molecular species is in an operation of an adsorption heat pump wherein water vapor is adsorbed by the microporous crystalline material. An embodiment of the invention is one, any or all of prior embodiments in this paragraph up through the second embodiment in this paragraph wherein the hydrocarbon conversion processes are selected from the group consisting of cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and a syngas shift process. An embodiment of the invention is one, any or all prior embodiments in this paragraph up through the embodiment in this paragraph wherein the separation of molecular species is based on the molecular size (kinetic diameter) or on the degree of polarity of the molecular species.

The invention claimed is:

1. A microporous crystalline material, AlPO-78 that has an empirical composition in an as-synthesized form and on an anhydrous basis expressed by an empirical formula:

$$R^+_r M_m^{2+} EP_x Si_y O_z$$

where M is at least one framework divalent cation and is selected from the group consisting of alkaline earth and transition metals, wherein M is a cation selected from the group consisting of beryllium, magnesium, cobalt (II), manganese, zinc, iron (II), nickel and mixtures thereof, R is an organoammonium cation, "r" is the mole ratio of R to E and varies from about 0.1 to about 2.0, "m" is the mole ratio of M to E and varies from 0 to about 1.0, "x" is a mole ratio of P to E and varies from 0.5 to about 2.0, a ratio of silicon to E is represented by "y" which varies from about 0 to about 1.0, E is a trivalent element which is tetrahedrally coordinated, is present in the framework, and is selected from the group consisting of aluminum, gallium, iron (III) and boron and "z" is a mole ratio of O to E and is given by an equation:

$$z=(2 \cdot m+r+3+5 \cdot x+4 \cdot y)/2$$

and is characterized by a following x-ray diffraction pattern, having at least the d-spacings and relative intensities set forth in Table 1:

TABLE 1

| 2-Theta | d(Å) | Intensity |
|---|---|---|
| 7.88-7.98 | 11.21-11.07 | m-s |
| 8.15-8.50 | 10.84-10.39 | m-s |
| 8.82-9.05 | 10.01-9.76 | s |
| 9.67-9.96 | 9.14-8.87 | s-vs |
| 10.58-10.81 | 8.35-8.17 | m |
| 10.92-11.71 | 8.09-7.55 | m-s |
| 13.21-13.67 | 6.69-6.47 | s |
| 14.10-14.54 | 6.27-6.08 | s-vs |
| 15.48-16.02 | 5.72-5.53 | m |
| 16.05-16.24 | 5.52-5.45 | s |
| 16.44-16.81 | 5.39-5.28 | m |
| 16.87-17.01 | 5.25-5.21 | m-s |
| 17.19-17.43 | 5.15-5.08 | s |
| 17.78-18.46 | 4.98-4.80 | s-vs |
| 18.73-19.22 | 4.73-4.61 | vw-w |
| 19.48-19.86 | 4.55-4.47 | w-m |
| 20.47-20.96 | 4.33-4.23 | s |
| 21.00-21.45 | 4.23-4.14 | m-s |
| 21.52-21.73 | 4.12-4.08 | m-s |
| 21.88-22.10 | 4.06-4.02 | s |
| 22.15-22.42 | 4.01-3.96 | m-s |
| 22.52-22.95 | 3.94-3.87 | w-m |
| 23.14-23.52 | 3.84-3.78 | w-m |
| 23.58-23.71 | 3.77-3.75 | s |
| 23.75-24.01 | 3.74-3.70 | w-m |
| 24.75-24.93 | 3.59-3.57 | w-m |
| 25.01-25.47 | 3.56-3.49 | vs |
| 26.15-26.31 | 3.40-3.38 | w-m |
| 26.37-26.54 | 3.38-3.35 | m |
| 26.78-27.02 | 3.33-3.30 | w-m |
| 27.11-27.40 | 3.29-3.25 | m |
| 28.39-28.86 | 3.14-3.09 | w-m |
| 29.22-29.65 | 3.05-3.01 | m |
| 30.60-30.95 | 2.92-2.89 | w-m |
| 31.62-31.93 | 2.83-2.80 | w-m |
| 31.97-32.28 | 2.80-2.77 | w-s |
| 32.44-32.89 | 2.76-2.72 | w-m |
| 33.19-33.40 | 2.70-2.68 | vw-w |
| 33.51-33.82 | 2.67-2.65 | w-m |
| 34.72-35.08 | 2.58-2.55 | vw-w. |

2. The microporous crystalline material of claim 1 wherein after being calcined said AlPO-78 material is characterized by the x-ray diffraction pattern, having at least the d-spacings and relative intensities set forth in Table 2 below:

TABLE 2

| 2-Theta | d(Å) | Intensity |
|---|---|---|
| 8.02-8.12 | 11.01-10.88 | w |
| 8.40-8.51 | 10.51-10.38 | m |
| 8.63-8.73 | 10.23-10.12 | w-m |
| 9.78-9.89 | 9.03-8.93 | m-s |
| 10.70-10.81 | 8.26-8.17 | m-s |
| 12.83-12.95 | 6.89-6.82 | vw |
| 13.71-13.86 | 6.45-6.38 | vs |
| 14.00-14.13 | 6.32-6.26 | m-s |
| 16.16-16.64 | 5.48-5.32 | vw-w |
| 16.92-17.05 | 5.23-5.19 | vw-w |
| 17.44-17.56 | 5.08-5.04 | m |
| 17.79-17.93 | 4.98-4.94 | m-s |
| 19.68-19.89 | 4.51-4.46 | w |
| 20.43-20.61 | 4.34-4.30 | w-m |
| 21.17-21.35 | 4.19-4.16 | w-m |
| 21.81-21.99 | 4.07-4.04 | m-s |
| 22.15-22.53 | 4.01-3.94 | m-s |
| 22.55-22.74 | 3.94-3.91 | w-m |
| 23.95-24.25 | 3.71-3.67 | m-s |
| 24.57-24.79 | 3.62-3.59 | m-s |
| 25.87-26.31 | 3.44-3.38 | w-m |
| 26.49-26.71 | 3.36-3.33 | m |
| 27.40-27.88 | 3.25-3.20 | m-s |
| 28.32-28.52 | 3.15-3.13 | m-s |
| 28.85-29.02 | 3.09-3.07 | vw-w |
| 29.40-29.63 | 3.03-3.01 | w-m |
| 29.71-29.93 | 3.00-2.98 | vw |
| 30.28-30.44 | 2.95-2.93 | vw-w |
| 31.21-31.38 | 2.86-2.85 | vw-w |
| 32.18-32.50 | 2.79-2.75 | w-m |
| 32.65-32.92 | 2.74-2.72 | w-m |
| 33.00-33.15 | 2.71-2.70 | w-m |
| 34.25-34.41 | 2.61-2.60 | vw-w |
| 35.16-35.35 | 2.55-2.54 | w-m. |

3. The microporous crystalline material of claim 1 characterized on an anhydrous basis by the empirical formula:

$$H_w M_m^{2+} EP_x Si_y O_z$$

where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, H is a proton, w" is the mole ratio of H to E and varies from 0 to 2.5, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0.05 to about 1.0, "m"+"y"≥0.1, and "z" is the mole ratio of O to E and has a value determined by the equation:

$$z=(w+2 \cdot m+3+5 \cdot x+4 \cdot y)/2.$$

4. The microporous crystalline material of claim 1 that indexes on a unit cell with hexagonal axes with lattice parameters a=12.768 Å and c=60.825 Å and has an ABC-6 net structure with the stacking sequence repeating every 24 layers along the c-axis (p=60.825/2.5=24.33).

5. A method of making a AlPO-78 microporous crystalline material comprising preparing a reaction mixture containing reactive sources described in terms of molar ratios of the oxides by a formula:

$$aR_2O:bMO:E_2O_3:cP_2O_5:dSiO_2:eH_2O$$

where "a" varies from about 0.75 to about 16, "b" varies from about 0 to about 2, "c" varies from about 0.8 to about 8, "d" varies from about 0 to about 4, and "e" varies from 30 to 800 wherein reactive sources of R, E, phosphorus and one or both M and silicon; reacting the reaction mixture at a temperature from about 60° C. to about 200° C. for a period of about 1 day to about 21 days; and isolating a solid product from a heterogeneous mixture wherein the AlPO-78 microporous material, is characterized by the x-ray following diffraction pattern, having at least the d-spacings and relative intensities set forth in Table 1:

TABLE 1

| 2-Theta | d(Å) | Intensity |
|---|---|---|
| 7.88-7.98 | 11.21-11.07 | m-s |
| 8.15-8.50 | 10.84-10.39 | m-s |
| 8.82-9.05 | 10.01-9.76 | s |
| 9.67-9.96 | 9.14-8.87 | s-vs |
| 10.58-10.81 | 8.35-8.17 | m |
| 10.92-11.71 | 8.09-7.55 | m-s |
| 13.21-13.67 | 6.69-6.47 | s |
| 14.10-14.54 | 6.27-6.08 | s-vs |
| 15.48-16.02 | 5.72-5.53 | m |
| 16.05-16.24 | 5.52-5.45 | s |
| 16.44-16.81 | 5.39-5.28 | m |
| 16.87-17.01 | 5.25-5.21 | m-s |
| 17.19-17.43 | 5.15-5.08 | s |
| 17.78-18.46 | 4.98-4.80 | s-vs |
| 18.73-19.22 | 4.73-4.61 | vw-w |
| 19.48-19.86 | 4.55-4.47 | w-m |
| 20.47-20.96 | 4.33-4.23 | s |
| 21.00-21.45 | 4.23-4.14 | m-s |
| 21.52-21.73 | 4.12-4.08 | m-s |
| 21.88-22.10 | 4.06-4.02 | s |
| 22.15-22.42 | 4.01-3.96 | m-s |
| 22.52-22.95 | 3.94-3.87 | w-m |
| 23.14-23.52 | 3.84-3.78 | w-m |
| 23.58-23.71 | 3.77-3.75 | s |
| 23.75-24.01 | 3.74-3.70 | w-m |
| 24.75-24.93 | 3.59-3.57 | w-m |
| 25.01-25.47 | 3.56-3.49 | vs |
| 26.15-26.31 | 3.40-3.38 | w-m |
| 26.37-26.54 | 3.38-3.35 | m |
| 26.78-27.02 | 3.33-3.30 | w-m |
| 27.11-27.40 | 3.29-3.25 | m |
| 28.39-28.86 | 3.14-3.09 | w-m |
| 29.22-29.65 | 3.05-3.01 | m |
| 30.60-30.95 | 2.92-2.89 | w-m |
| 31.62-31.93 | 2.83-2.80 | w-m |
| 31.97-32.28 | 2.80-2.77 | w-s |
| 32.44-32.89 | 2.76-2.72 | w-m |
| 33.19-33.40 | 2.70-2.68 | vw-w |
| 33.51-33.82 | 2.67-2.65 | w-m |
| 34.72-35.08 | 2.58-2.55 | vw-w. |

6. The method of claim 5 wherein the AlPO-78 is calcined at a temperature of at least 550° C. and is characterized by the x-ray diffraction pattern, having at least the d-spacings and relative intensities set forth in Table 2 below:

TABLE 2

| 2-Theta | d(Å) | Intensity |
|---|---|---|
| 8.02-8.12 | 11.01-10.88 | w |
| 8.40-8.51 | 10.51-10.38 | m |
| 8.63-8.73 | 10.23-10.12 | w-m |
| 9.78-9.89 | 9.03-8.93 | m-s |
| 10.70-10.81 | 8.26-8.17 | m-s |
| 12.83-12.95 | 6.89-6.82 | vw |
| 13.71-13.86 | 6.45-6.38 | vs |
| 14.00-14.13 | 6.32-6.26 | m-s |
| 16.16-16.64 | 5.48-5.32 | vw-w |
| 16.92-17.05 | 5.23-5.19 | vw-w |
| 17.44-17.56 | 5.08-5.04 | m |
| 17.79-17.93 | 4.98-4.94 | m-s |
| 19.68-19.89 | 4.51-4.46 | w |

TABLE 2-continued

| 2-Theta | d(Å) | Intensity |
|---|---|---|
| 20.43-20.61 | 4.34-4.30 | w-m |
| 21.17-21.35 | 4.19-4.16 | w-m |
| 21.81-21.99 | 4.07-4.04 | m-s |
| 22.15-22.53 | 4.01-3.94 | m-s |
| 22.55-22.74 | 3.94-3.91 | w-m |
| 23.95-24.25 | 3.71-3.67 | m-s |
| 24.57-24.79 | 3.62-3.59 | m-s |
| 25.87-26.31 | 3.44-3.38 | w-m |
| 26.49-26.71 | 3.36-3.33 | m |
| 27.40-27.88 | 3.25-3.20 | m-s |
| 28.32-28.52 | 3.15-3.13 | m-s |
| 28.85-29.02 | 3.09-3.07 | vw-w |
| 29.40-29.63 | 3.03-3.01 | w-m |
| 29.71-29.93 | 3.00-2.98 | vw |
| 30.28-30.44 | 2.95-2.93 | vw-w |
| 31.21-31.38 | 2.86-2.85 | vw-w |
| 32.18-32.50 | 2.79-2.75 | w-m |
| 32.65-32.92 | 2.74-2.72 | w-m |
| 33.00-33.15 | 2.71-2.70 | w-m |
| 34.25-34.41 | 2.61-2.60 | vw-w |
| 35.16-35.35 | 2.55-2.54 | w-m. |

7. The method of claim 5 wherein the sources of aluminum are selected from the group consisting of aluminum alkoxides, precipitated aluminas, aluminum metal, aluminum hydroxide, aluminum salts and alumina sols.

8. The method of claim 5 wherein sources of phosphorus are selected from the group consisting of orthophosphoric acid, phosphorus pentoxide, and ammonium dihydrogen phosphate.

9. The method of claim 5 wherein sources of silica are selected from the group consisting of tetraethylorthosilicate, colloidal silica, and precipitated silica.

10. The method of claim 5 wherein sources of E elements are selected from the group consisting of organoammonium borates, boric acid, precipitated gallium oxyhydroxide, gallium sulfate, ferric sulfate, and ferric chloride.

11. The method of claim 5 wherein sources of the M metals are selected from the group consisting of halide salts, nitrate salts, acetate salts, and sulfate salts of the respective alkaline earth and transition metals.

12. The method of claim 5 wherein R is an organoammonium cation prepared from a reaction of an aqueous mixture of a cyclic secondary amine and an organic dihalide.

13. The method of claim 12 wherein the cyclic secondary amines are selected from the group consisting of piperidine, homopiperidine, pyrrolidine, and morpholine.

14. The method of claim 6 wherein the AlPO-78 microporous crystalline material is calcined at a temperature of at least 600° C.

15. A process of separating mixtures of molecular species, removing contaminants or catalyzing hydrocarbon conversion processes comprising contacting a feed stream with a microporous crystalline material, AlPO-78 that has an empirical composition in a calcined form and on an anhydrous basis expressed by an empirical formula:

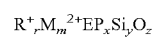

$$R^+_r M_m^{2+} E P_x Si_y O_z$$

where M is at least one framework divalent cation and is selected from the group consisting of alkaline earth and transition metals, wherein M is a cation selected from the group consisting of beryllium, magnesium, cobalt (II), manganese, zinc, iron (II), nickel and mixtures thereof, R is an organoammonium cation, "r" is the mole ratio of R to E and varies from about 0.1 to about 2.0, "m" is the mole ratio of M to E and varies from 0 to about 1.0, "x" is a mole ratio of P to E and varies from 0.5 to about 2.0, a ratio of silicon to E is represented by "y" which varies from about 0 to about 1.0, E is a trivalent element which is tetrahedrally coordinated, is present in the framework, and is selected from the group consisting of aluminum, gallium, iron (III) and boron and "z" is a mole ratio of O to E and is given by an equation:

$$z=(2 \cdot m+r+3+5 \cdot x+4 \cdot y)/2$$

and is characterized by an x-ray following diffraction pattern, having at least the d-spacings and relative intensities set forth in Table 2:

TABLE 2

| 2-Theta | d(Å) | Intensity |
|---|---|---|
| 8.02-8.12 | 11.01-10.88 | w |
| 8.40-8.51 | 10.51-10.38 | m |
| 8.63-8.73 | 10.23-10.12 | w-m |
| 9.78-9.89 | 9.03-8.93 | m-s |
| 10.70-10.81 | 8.26-8.17 | m-s |
| 12.83-12.95 | 6.89-6.82 | vw |
| 13.71-13.86 | 6.45-6.38 | vs |
| 14.00-14.13 | 6.32-6.26 | m-s |
| 16.16-16.64 | 5.48-5.32 | vw-w |
| 16.92-17.05 | 5.23-5.19 | vw-w |
| 17.44-17.56 | 5.08-5.04 | m |
| 17.79-17.93 | 4.98-4.94 | m-s |
| 19.68-19.89 | 4.51-4.46 | w |
| 20.43-20.61 | 4.34-4.30 | w-m |
| 21.17-21.35 | 4.19-4.16 | w-m |
| 21.81-21.99 | 4.07-4.04 | m-s |
| 22.15-22.53 | 4.01-3.94 | m-s |
| 22.55-22.74 | 3.94-3.91 | w-m |
| 23.95-24.25 | 3.71-3.67 | m-s |
| 24.57-24.79 | 3.62-3.59 | m-s |
| 25.87-26.31 | 3.44-3.38 | w-m |

TABLE 2-continued

| 2-Theta | d(Å) | Intensity |
|---|---|---|
| 26.49-26.71 | 3.36-3.33 | m |
| 27.40-27.88 | 3.25-3.20 | m-s |
| 28.32-28.52 | 3.15-3.13 | m-s |
| 28.85-29.02 | 3.09-3.07 | vw-w |
| 29.40-29.63 | 3.03-3.01 | w-m |
| 29.71-29.93 | 3.00-2.98 | vw |
| 30.28-30.44 | 2.95-2.93 | vw-w |
| 31.21-31.38 | 2.86-2.85 | vw-w |
| 32.18-32.50 | 2.79-2.75 | w-m |
| 32.65-32.92 | 2.74-2.72 | w-m |
| 33.00-33.15 | 2.71-2.70 | w-m |
| 34.25-34.41 | 2.61-2.60 | vw-w |
| 35.16-35.35 | 2.55-2.54 | w-m. |

16. The process of claim 15 wherein the separation of molecular species is in an operation of an adsorption heat pump wherein water vapor is adsorbed by said microporous crystalline material.

17. The process of claim 15 wherein said hydrocarbon conversion processes are selected from the group consisting of cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and a syngas shift process.

18. The process of claim 15 wherein said separation of molecular species is based on the molecular size (kinetic diameter) or on the degree of polarity of the molecular species.

\* \* \* \* \*